United States Patent [19]

Jones et al.

[11] Patent Number: 4,954,350
[45] Date of Patent: Sep. 4, 1990

[54] PHARMACEUTICAL FORMULATIONS CONTAINING ACRIVASTINE

[75] Inventors: Harry P. Jones; Robert J. Mackey; Michael J. D. Gamlen, all of Dartford, England

[73] Assignee: Burroughs Wellcome Co., Research Triangle Park, N.C.

[21] Appl. No.: 355,142

[22] Filed: May 15, 1989

Related U.S. Application Data

[63] Continuation of Ser. No. 173,262, Mar. 25, 1988, abandoned.

[30] Foreign Application Priority Data

Mar. 27, 1987 [GB] United Kingdom ............... 8707416

[51] Int. Cl.$^5$ ............................................. A61K 9/16
[52] U.S. Cl. ................................. 424/493; 424/461; 424/462; 424/470; 424/495; 424/497
[58] Field of Search ............... 424/490, 495, 493, 497, 424/461, 462, 460, 470; 514/343, 849, 929, 853, 850, 855, 277, 331, 317, 326

[56] References Cited

U.S. PATENT DOCUMENTS

| 4,501,893 | 2/1985 | Findlay et al. ............ 546/281 |
| 4,650,807 | 3/1987 | Findlay et al. ............ 514/343 |
| 4,693,896 | 9/1987 | Wheatley et al. .......... 424/480 |
| 4,871,733 | 10/1989 | Sunshine et al. .......... 514/212 |

FOREIGN PATENT DOCUMENTS

| 0085959 | 8/1983 | European Pat. Off. . |
| 0142877 | 5/1985 | European Pat. Off. . |
| 0202051 | 11/1986 | European Pat. Off. . |
| 0205336 | 12/1986 | European Pat. Off. . |
| 0226884 | 7/1987 | European Pat. Off. . |
| 0248447 | 12/1987 | European Pat. Off. . |
| 0249949 | 12/1987 | European Pat. Off. . |
| 0250267 | 12/1987 | European Pat. Off. . |
| WO85/03436 | 8/1985 | PCT Int'l Appl. . |
| WO85/03437 | 8/1985 | PCT Int'l Appl. . |
| WO87/01588 | 3/1987 | PCT Int'l Appl. . |
| WO87/02240 | 4/1987 | PCT Int'l Appl. . |
| 2086725 | 5/1982 | United Kingdom . |
| 2087235 | 5/1982 | United Kingdom . |
| 2157170 | 10/1985 | United Kingdom . |
| 2178313 | 2/1987 | United Kingdom . |
| 2180154 | 3/1987 | United Kingdom . |

*Primary Examiner*—Thurman K. Page
*Attorney, Agent, or Firm*—Donald Brown

[57] ABSTRACT

The invention relates to a controlled release pharmaceutical formulation for oral administration which comprises discrete units comprising acrivastine or a salt thereof coated with a mixture containing:

(a) a copolymer or polymer containing repeating monomer units selected from alkyl esters of acrylic and methacrylic acids and
(b) ethyl cellulose, and a process for preparing such formulations.

12 Claims, No Drawings

PHARMACEUTICAL FORMULATIONS CONTAINING ACRIVASTINE

This is a continuation of co-pending application Ser. No. 07/173,262 filed on Mar. 25, 1988 now abandoned.

The present invention relates to novel pharmaceutical formulations, in particular to controlled release formulations containing Acrivastine as the active ingredient.

Acrivastine is the approved name of the compound (E)-3-[6-[(E)-3-(1-pyrrolidinyl)-1-(p-tolyl)-1-propenyl]-2-pyridyl] acrylic acid, which has the structural formula:

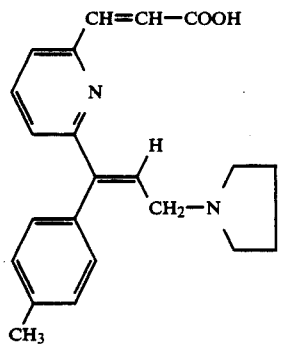

This compound is disclosed in our European Patent Application Specification No. 85959.

Acrivastine has potent anti-histamine activity whilst being substantially free from the sedative effects usually associated with antihistamines, such as brompheniramine, chlorpheniramine and triprolidine. It may therefore advantageously be used in the treatment of a variety of conditions such as are described in EPA specification No. 85959 including the relief of the symptoms of nasal stuffiness due to colds and vasomotor rhinitis, and for the symptomatic control of allergic conditions.

For use in medicine, acrivastine may if desired be administered in the form of a pharmacologically and pharmaceutically acceptable salt. Such salts include but are not limited to acid addition salts such as those formed with hydrochloric, sulphuric nitric, phosphonic, maleic, salicylic, toluene-p-sulphonic, tartaric, citric, methanesulphonic, formic, malonic, isethionic, succinic, naphthalene-2-sulphonic and benzenesulphonic acid, and alkali metal or alkaline earth metal salts such as the sodium, potassium or calcium salts of the carboxylic acid. Unless indicated otherwise, references in this specification to acrivastine include a reference to its pharmaceutically and pharmacologically acceptable salts. A particularly preferred salt for the purpose of the present invention is the hydrochloride.

Acrivastine may be administered by a variety of routes, but is conveniently administered by oral administration. Thus, we have found that oral administration of an 8 mg dose of acrivastine, formulated in conventional manner, to adult human volunteers will typically provide therapeutic levels of acrivastine in the blood for up to approximately 8 hours. Hence conventional formulations of acrivastine will preferably be administered in three daily doses to provide continuous relief of symptoms.

Whilst acrivastine exhibits a useful duration of action, it would nevertheless be desirable to administer acrivastine as a controlled release formulation in order to extend the duration of action of the drug, and hence reduce the frequency of dosing, without increasing the overall daily dose. It would also be desirable for such a controlled release formulation to provide relatively uniform levels of acrivastine in the body. However, in order to maximise the bioavailability it has been found that the rate of release should not be too slow. Preferably the acrivastine should be released within 3-4 hours of administration.

It is generally known in the pharmaceutical formulation art that the release of active substances from pharmaceutical compositions may be delayed by formulating the active ingredient in a matrix, or by film coating the active ingredient, and a wide variety of release-delaying substances for use in such matrices or film coats are known. However it is also known that the rate of release is dependent not only on the nature of the film coat or matrix-forming agent, but also on the nature of the active ingredient and excipients, and on interactions between them. Thus it is generally not possible to predict the release profile of a particular formulation.

UK Patent Application No. 2087235A discloses a granular delayed-release formulation containing granulated or crystalline active substances coated with a homogenous mixture of a polyacrylate insoluble but dispersible in water (such as Eudragit E30D) and a cellulose ether insoluble but dispersible in water (such as Aquacoat ECD30). The two components of the coating mixture are said to be preferably used in a ratio of 2.5:1 to 5:1 (polyacrylate:cellulose ether). The only active substances specifically disclosed in this specification are potassium chloride, lithium salts, diclofenac sodium and pirprofen.

UK Patent Application Nos. 2086725A and 2157170A disclose respectively quick-disintegrating pressed shapes and storage stable, quick-disintegrating pressed shapes containing the aforementioned coated granules. In each case the components of the coating mixture are used in a ratio of 2.5:1 to 5:1 (polyacrylate:cellulose ether).

UK Patent Application No. 2178313A describes a process for preparing film-coated granular delayed release forms similar to those disclosed in the above specifications. However, in this specification the ratio of polyacrylate:ethylcellulose in the coating mixture may be in a ratio of from 20:1 to 1:5. The preferred ratio is said to be in range 20:1 to 1:1, particularly 9:1 to 4:1 e.g. 5:1. In the majority of the working examples the components of the coating mixture, Eudragit E30D and Aquacoat ECD30, are used in a ratio of 5:1 or above. In one example these components are used in a 1:1 ratio. However in this and all the other examples a further coating of Aquacoat ECD30 alone is added. The active ingredient to which the aforementioned coatings are applied include proxyphilline, diprophylline, theophylline, potassium chloride, dimethindene, sodium fluoride, 1,1-diphenyl-3-(N-piperidino)-1-propanol methanesulphonate and Venoruton. These is no disclosure of active ingredients similar to those disclosed in EP 85859.

We have now surprisingly found that when acrivastine is coated with a mixture of a non-ionic polymer based on poly(meth)acrylic acid esters and a latex dispersion of ethyl cellulose the resulting formulation advantageously provides sustained and controlled release of acrivastine during its passage through the gastrointestinal tract.

The present invention therefore provides controlled release pharmaceutical formulations for oral administration wherein discrete units comprising acrivastine or a salt thereof are coated with a mixture containing:
(a) a polymer or copolymer containing repeating monomer units selected from alkyl esters of acrylic and methacrylic acids and
(b) ethyl cellulose In the coating of formulations according to the present invention component (a) is preferably a copolymer of one or more $C_{1-4}$ alkyl esters of acrylic and/or methacrylic acid e.g. methyl or ethyl acrylate. Such polymers typically have an average molecular weight in the range 100,000 to 950,000. Particular examples of such polymers include those available under the trade names Eudragit E30D (in the form of an aqueous dispersion) from Rohm Pharma GmbH (Darmstadt, West Germany) and Scopacryl D340, from AHP Chemie (East Germany). Thus, for example, Eudragit E30D has an average molecular weight of 800,000. Component (b) of the coating is preferably employed in the form of an aqueous latex dispersion. Suitable latex dispersions of ethyl cellulose include those available under the trade names Aquacoat ECD-30 from FMC Corporation (Philadelphia, USA) and Surelease from Colorcon (West Point, Penn.).

The components (a) and (b) will generally be present in the coating mixture in a weight ratio in the range 2:1 to 1:2, preferably 1.5:1 to 1:1.5 most preferably 1:1.

In addition to the components (a) and (b) described above, the controlled release coating may include other appropriate excipients, such as anti-agglomerating agents (e.g. talc, kaolin or colloidal silica e.g. Aerosil) to prevent sticking of the coated cores and/or agents for modifying the permeability or porosity of the coating such as electrolytes (e.g. sodium chloride) polyethylene glycols, lactose, sucrose or mannitol. Such excipients typically comprise between 5 and 40% by weight of the coat. A particularly preferred excipient is mannitol.

The above-mentioned discrete units generally take the form of cores comprising acrivastine optionally in admixture with one or more pharmaceutical carriers or excipients. Examples of such carriers or excipients are well know in the pharmaceutical art for the formulation of tablets and granules and include for example binders, lubricants, inert diluents, surface active agents and dispersing agents. Such cores may be prepared for example by admixing acrivastine and any appropriate carriers or excipients and compressing or moulding the resulting mixture. Alternatively, the acrivastine can be applied to an inert core e.g. a non-pareil or prill optionally in admixture with one or more appropriate excipients, for example in a solution of a binder such as polyvinylpyrrolidone, followed by drying. The solution of acrivastine applied to the core may conveniently be acidified, e.g. with hydrochloric acid. The solution may also contain one or more suitable solvents, for example an aqueous alcohol such as ethanol or isopropyl alcohol.

A further alternative form for the core is the formulation of acrivastine with one or more appropriate excipients to produce so-called spheroids i.e., spherical particles having a diameter of 0.5 to 2 mm. Such spheroids are known in the art, for example as described by A. D. Reynolds, Manufacturing Chemists Aerosol News, Jun. 1970 pages 40-43. Such spheroids may be produced by mixing the active ingredient with water and any appropriate excipients to form an extrudable mass which is then extruded as elongate particles and converted into spheroids for example by use of a spheroniser containing a rotating plate on which the elongate particles are converted by the rotary motion of the plate into spherical particles, followed by sieving to remove particles which are too fine or too coarse. The spheriods may be packaged as such, e.g. in a sachet, for suspension in water before administration or to be sprinkled on food, or incorporated into a capsule or tablet.

The coatings may be applied to the discrete units of acrivastine in conventional manner. Thus for example the polymer and any other coating components may be suspended in an appropriate liquid medium e.g. water to form a dispersion of the polymer. The dispersion may then be applied to the discrete units by spray coating for example in a fluid bed, to form a coating of the desired thickness. Other methods of applying the coatings include pan coating. Following application of the coating the coated units may be heated to "cure" the film. The coated units are advantageously heated in the range 30°-100° C., preferably 50°-80° C. e.g. 70° C. The heating will generally be effected for between 0.25 and 3 hours e.g. 0.5 to 2 hours.

If desired, further acrivastine may be applied to the outside of the coated units. This may be achieved for example in a similar manner to the application of acrivastine to an inert core, as hereinbefore described. The coated units generally contain between 5 and 25% by weight of acrivastine. The coating typically constitutes 1 to 15% by weight of the total formulation.

The coated discrete units of acrivastine according to the present invention are preferably presented in a unit dose form, e.g. a tablet or a capsule. Such unit dose forms may if appropriate comprise coated discrete units of acrivastine in admixture with pharmaceutically acceptable carriers of excipients such as those described above. Alternatively or additionally the coated units may be admixed with other therapeutic agents, for example sympathomimetic agents such as the decongestant pseudoephedrine, an antitussive such as codeine, an analgesic, an antiinflammatory, an antipyretic or an expectorant. Such additional therapeutic agents may be in a form intended for immediate release or they may themselves be formulated for controlled release.

The formulations according to the present invention may be used to treat a variety of conditions, such as those described in EPA Specification No. 85959. Thus, for example, the formulations may be employed to relieve symptoms of nasal stuffiness due to colds and vasomotor rhinitis and for the symptomatic control of allergic conditions including nasal allergy, perennial rhinitis, urticaria, angioneurotic oedema, allergic conjunctivitis, food allergy, drug and serum reactions, insect bites and stings and desensitizing reactions. The formulations may also be used in conditions responsive to the antipruritic activity of acrivastine including allergic dermatoses, neurodermatitis, anogenital pruritus, and pruritus of non-specific origin such as eczema, and of specific cause such as chickenpox, photosensitivity and sunburn.

The amount of acrivastine required to treat the above conditions will depend upon the nature and severity of the condition to be treated. A typical oral dose of acrivastine for an adult human of average bodyweight (around 70 kg) is in the range 0.05 to 1.0 mg/kg per day, preferably 0.1 to 0.5 mg/kg per day, most preferably 0.3-0.4 mg/kg per day.

The total daily dose of acrivastine provided by the formulations of the present invention may be presented as divided units doses, which may be administered for example from one to six times per day. A unit dose according to the present invention conveniently contains half the total daily dosage of acrivastine, thus permitting twice-daily dosing. A typical unit dose according to the present invention will preferably contain from 1 to 20 mg of acrivastine preferably 5–15 mg, most preferably about 12 mg.

The invention will now be further illustrated by the following non-limiting examples.

In the Examples dissolution of the encapsulated material was measured by the method of the U.S. Pharmacopoeia (21st Edition, 1985) using Apparatus 2. The initial dissolution medium was 0.1M hydrochloric acid; after 30 minutes the pH was adjusted to 7.0 and testing continued for 4 hours.

EXAMPLE 1

CONTROLLED RELEASE PELLETS

| Ingredients | mg | % |
|---|---|---|
| Acrivastine | 9.00 | 13.42 |
| Non-pareil | 53.01 | 79.06 |
| Polyvinyl pyrrolidone | 0.58 | 0.86 |
| Eudragit E30D | 1.03 | 1.54 |
| Aquacoat ECD30 | 1.03 | 1.54 |
| Mannitol | 1.11 | 1.66 |
| Hydrochloric acid (36%) | 0.95 | 1.41 |
| Talc | 0.34 | 0.51 |
| | 67.05 | 100 |

METHOD

The formulation was prepared according to the following general method:

The acrivastine and polyvinyl pyrrolidone were stirred in ethanol. The hydrochloric acid was diluted with water to give a 7% w/w solution and added slowly to the alcoholic suspension with constant stirring. Mixing was continued until all solid material had dissolved. The drug solution was sprayed on to the non-pareils in a fluid bed system. The mannitol was dissolved in water, and the Aquacoat and the Eudragit suspensions added with mixing. The polymeric suspension was sprayed on to the drug-coated non-pareils in a fluid bed system. The pellets were cured at 70° C. for 1 hour. The talc was distributed throughout the pellet bed and fluidised for a suitable time.

EXAMPLE 2

| Ingredient | Content per capsules | |
|---|---|---|
| | mg | % |
| Acrivastine | 12.00 | 14.03 |
| Non Pareil | 64.40 | 75.30 |
| Polyvinyl Pyrrolidone | 1.00 | 1.17 |
| Eudragit NE30D* | 1.22 | 1.43 |
| Aquacoat ECD30D | 1.22 | 1.43 |
| Mannitol | 1.31 | 1.53 |
| Hydrochloric acid (36%) | 3.98 | 4.65 |
| Talc | 0.39 | 0.46 |
| | 85.52 | 100.0 |

*Eudragit NE30D = Eudragit E30D

METHOD

The acrivastine and polyvinyl pyrrolidone were stirred in ethanol and acidified with hydrochoric acid to give a drug solution as described in Example 1. Three-quarters of this solution was sprayed onto the non-pareils in a fluid bed system. The non-pareils were coated with a suspension of a mixture of Aquacoat ECD30, Eudragit NE30D and mannitol, as described in Example 1, and the pellets were cured for 1 hour at 70° C. The remaining drug solution was then applied to the pellets which were dried at 50° C. The talc was distributed throughout the pellet bed and fluidised for a suitable time. The pellets were then filled into capsules.

| Dissolution Profile | |
|---|---|
| Time (mins) | % Dissolution |
| 60 | 64 |
| 120 | 79 |
| 180 | 87 |
| 240 | 92 |

EXAMPLE 3

| Ingredients | Content per capsule | |
|---|---|---|
| | mg | % |
| Acrivastine | 12.00 | 14.10 |
| Non-Pareil | 63.74 | 74.87 |
| Polyvinyl Pyrrolidone | 1.00 | 1.18 |
| Eudragit NE30D | 1.44 | 1.69 |
| Aquacoat ECD30 | 1.44 | 1.69 |
| Mannitol | 1.56 | 1.83 |
| Hydrochloric Acid (36% w/w) | 3.55 | 4.17 |
| Talc | 0.40 | 0.47 |
| | 85.13 | 100.0 |

METHOD

The coated pellets were prepared according to the method of Example 2.

| Dissolution Profile | |
|---|---|
| Time (mins) | Dissolution (%) |
| 60 | 61 |
| 120 | 85 |
| 180 | 94 |
| 240 | 99 |

EXAMPLE 4

| Ingredient | Content per capsule | |
|---|---|---|
| | mg | % |
| Acrivastine | 12.00 | 6.25 |
| Lactose | 108.90 | 56.70 |
| Sodium Starch Glycollate | 12.50 | 6.51 |
| Magnesium Stearate | 0.60 | 0.31 |
| Hydrochloric Acid (36% w/w) | 0.95 | 0.49 |
| Polyvinyl Pyrrolidone | 0.58 | 0.30 |
| Non-Pareil | 53.01 | 27.60 |
| Eudragit NE30D | 1.03 | 0.54 |
| Aquacoat ECD-30 | 1.03 | 0.54 |
| Mannitol | 1.11 | 0.58 |
| Talc | 0.34 | 0.18 |
| | 192.05 | 100.0 |

METHOD

Acrivastine controlled release pellets were prepared as described in Example 1 using 75% of the acrivatine and the pellets were mixed with the talc.

The remaining 25% acrivastine was blended with the lactose and sodium starch glycollate until a homogenous mixture was obtained and this was further blended with the magnesium stearate. The powder and pellets were then filled into capsules.

| Dissolution Profile | |
|---|---|
| Time (minutes) | Dissolution (%) |
| 60 | 67 |
| 120 | 78 |
| 180 | 85 |
| 240 | 93 |

EXAMPLE 5

| Ingredients | Content per capsule mg |
|---|---|
| *Acrivastine Controlled Release Pellets | 85.5 (Containing 12 mg Acrivastine) |
| Pseudoephedrine Controlled Release Pellets (Eurand) | 155.0 (Containing 90 mg Pseudoephedrine) |
| Talc | 1.2 |
| | 241.7 |

*Prepared as in Example 2

METHOD

The acrivastine and pseudoephedrine controlled release pellets were each blended with talc and the two components filled into capsules.

We claim:

1. A controlled release pharmaceutical formulation for oral administration which comprises discrete units comprising acrivastine or a pharmacologically and pharmaceutically acceptable salt thereof coated with a mixture containing:
   (a) a copolymer or polymer containing repeating monomer units selected from alkyl esters of acrylic and methacrylic acids and
   (b) ethyl cellulose.

2. A formulation according to claim 1 where coating component (a) is a copolymer of one or more $C_{1-4}$ alkyl esters of acrylic or methacrylic acid.

3. A formulation according to claim 2 wherein the co-polymer has an average molecular weight of between 100,000 and 950,000.

4. A formulation according to claim 1 wherein components (a) and (b) are present in the coating in a weight ratio of 2:1 to 1:2.

5. A formulation according to claim 1 wherein the components (a) and (b) are present in the coating in a weight ratio of 1:1.

6. A formulation according to claim 1 wherein the coating contains between 5 and 40% of an agent for modifying the porosity of the coating.

7. A formulation according to claim 6 wherein the agent for modifying the porosity of the coating is mannitol.

8. A formulation according to claim 1 wherein acrivastine is present as a hydrochloride salt.

9. A formulation according to claim 1 wherein the coated discrete units are presented in unit dose form.

10. A formulation according to claim 9 wherein the coated discrete units are admixed with a further therapeutic agent.

11. A formulation according to claim 10 wherein the further therapeutic agent is pseudoephedrine.

12. A process for preparing a formulation according to claim 1 which comprises applying to discrete units comprising acrivastine or a salt thereof a coating mixture containing
   (a) a polymer or copolymer containing repeating monomer units selected from alkyl esters of acrylic and methacrylic acids and
   (b) ethyl cellulose.

* * * * *